United States Patent
Patrick

(10) Patent No.: US 8,343,305 B2
(45) Date of Patent: Jan. 1, 2013

(54) METHOD AND APPARATUS FOR DIAGNOSING STATUS OF PARTS IN REAL TIME IN PLASMA PROCESSING EQUIPMENT

(75) Inventor: Roger Patrick, Mountain View, CA (US)

(73) Assignee: Lam Research Corporation, Fremont, CA (US)

( * ) Notice: Subject to any disclaimer, the term of this patent is extended or adjusted under 35 U.S.C. 154(b) by 1013 days.

(21) Appl. No.: 11/896,637

(22) Filed: Sep. 4, 2007

(65) Prior Publication Data

US 2009/0061542 A1 Mar. 5, 2009

(51) Int. Cl.
*C23C 16/00* (2006.01)
*C23F 1/00* (2006.01)
*H01L 21/306* (2006.01)

(52) U.S. Cl. ............... 156/345.24; 118/715; 118/728; 118/729; 118/730; 156/345.1; 156/345.23; 156/345.25; 156/345.51

(58) Field of Classification Search ............ 117/84, 117/85, 86, 200, 201, 202; 118/695, 696, 118/708, 715, 716, 723 R; 156/345.1, 345.13, 156/345.15, 345.24, 345.25, 345.26, 345.27, 156/345.28, 345.34; 216/58, 59, 60, 61, 216/83, 84, 85, 86; 427/446, 457, 585, 248.1; 438/14, 15, 16, 17, 18, 689
See application file for complete search history.

(56) References Cited

U.S. PATENT DOCUMENTS

| | | | |
|---|---|---|---|
| 4,662,975 A * | 5/1987 | Dufresne et al. | 156/345.15 |
| 5,221,416 A * | 6/1993 | Kishi et al. | 216/71 |
| 5,460,689 A | 10/1995 | Raaijmakers et al. | |
| 5,665,166 A | 9/1997 | Deguchi et al. | |
| 5,824,607 A | 10/1998 | Trow et al. | |
| 5,947,053 A | 9/1999 | Burnham et al. | |
| 6,332,961 B1 | 12/2001 | Johnson et al. | |
| 6,394,023 B1 | 5/2002 | Crocker | |
| 6,458,239 B1 * | 10/2002 | Bhardwaj et al. | 156/345.24 |
| 6,562,187 B2 | 5/2003 | Winniczek et al. | |
| 6,663,791 B1 | 12/2003 | Kawaguchi | |
| 6,806,949 B2 | 10/2004 | Ludviksson et al. | |
| 6,894,769 B2 | 5/2005 | Ludviksson et al. | |
| 6,902,646 B2 | 6/2005 | Mahoney et al. | |
| 6,943,568 B2 * | 9/2005 | Maeno | 324/686 |
| 6,957,622 B2 | 10/2005 | Boettcher et al. | |
| 7,064,812 B2 | 6/2006 | Ludviksson et al. | |
| 7,110,110 B2 | 9/2006 | Fink | |

(Continued)

OTHER PUBLICATIONS

Wikipedia entry for voltmeter. Performed and printed on Feb. 20, 2009 from http://en.wikipedia.org/wiki/Voltmeter.*
International Search Report and Written Opinion mailed Jan. 30, 2009 for PCT/US2008/010070.

*Primary Examiner* — Parviz Hassanzadeh
*Assistant Examiner* — Tiffany Nuckols
(74) *Attorney, Agent, or Firm* — Buchanan Ingersoll & Rooney PC

(57) ABSTRACT

Apparatus and methods for diagnosing status of a consumable part of a plasma reaction chamber, the consumable part including at least one conductive element embedded therein. The method includes the steps of: coupling the conductive element to a power supply so that a bias potential relative to the ground is applied to the conductive element; exposing the consumable part to plasma erosion until the conductive element draws a current from the plasma upon exposure of the conductive element to the plasma; measuring the current; and evaluating a degree of erosion of the consumable part due to the plasma based on the measured current.

13 Claims, 3 Drawing Sheets

U.S. PATENT DOCUMENTS

| | | |
|---|---|---|
| 7,122,480 B2 | 10/2006 | Li et al. |
| 7,158,848 B2 | 1/2007 | Tanaka et al. |
| 2003/0022397 A1 | 1/2003 | Hess et al. |
| 2003/0145950 A1* | 8/2003 | Hirose .................... 156/345.43 |
| 2004/0053428 A1 | 3/2004 | Steger |
| 2005/0213079 A1* | 9/2005 | Fink ............................... 356/72 |
| 2005/0284570 A1* | 12/2005 | Doran et al. ............. 156/345.24 |
| 2006/0171848 A1 | 8/2006 | Roche et al. |

* cited by examiner

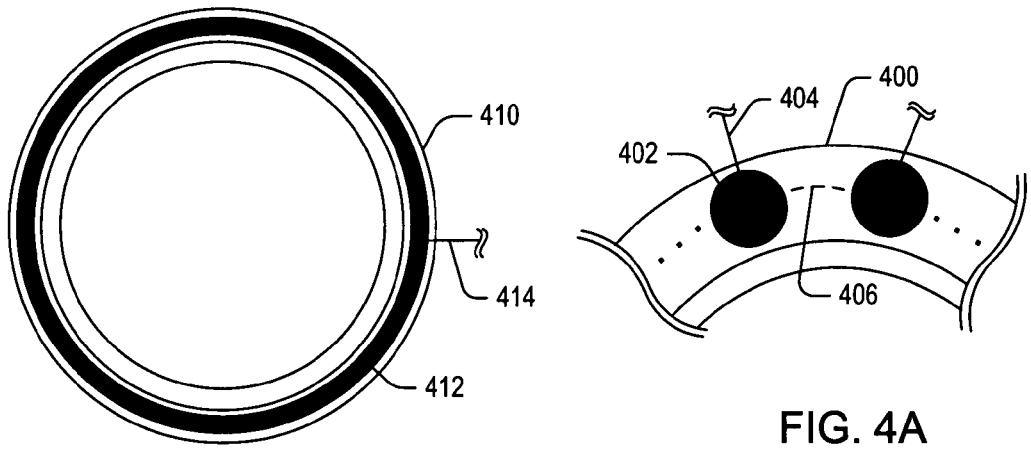
FIG. 4B
FIG. 4A
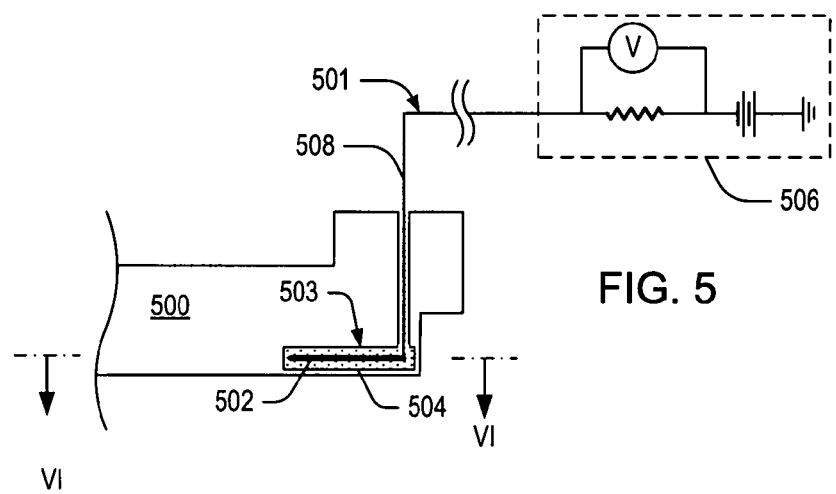
FIG. 5
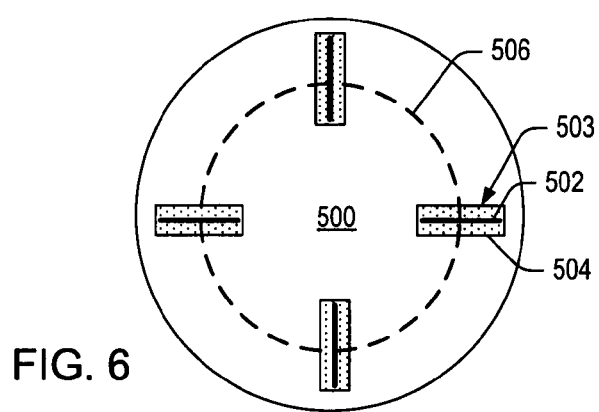
FIG. 6

METHOD AND APPARATUS FOR DIAGNOSING STATUS OF PARTS IN REAL TIME IN PLASMA PROCESSING EQUIPMENT

BACKGROUND

Plasma has been used in many applications, such as semiconductor processing steps. A conventional plasma processing equipment generates plasma having harsh thermal and/or chemical properties, which causes wear to numerous parts that are exposed thereto during the processing steps. Due to the aggressive nature of the plasma, repeated contact with the plasma may cause one or more of the parts to erode gradually and/or fail abruptly, degrading the performance of the equipment and causing the process result to change over time.

As such, it is important to carefully monitor the states of these parts and change the parts at the appropriate time. If they are changed too soon, the production cost is increased by throwing away the parts which could still be used further. If they are left too long before changing, damage may result to other parts of the equipment leading to additional cost. For instance, eroding an edge ring in a semiconductor processing chamber beyond the safe limit may result in destroying an electrostatic chuck which is a far more costly part. The ideal case is to use the part to the maximum safe limit and no further.

The useful lifetime of each part may be estimated through statistical analysis of degradation and failure when placed in specific environments. However, it is always possible that the part may fail or need to be replaced earlier than expected. Also, in practice, the lifetime of the part may depend on exactly how the equipment is run, which may not be known or closely monitored. Furthermore, it may be necessary to open the equipment to perform an inspection, which is disruptive to production and leads to a certain down-time. Thus, it would be desirable to provide an ability to detect events indicative of the end of useful lifetime, faults, or failure of the part during the operation of the equipment and independent of application in any specific plasma process. It would be further desirable to provide an ability to monitor the state of each part in real time and calling of an alarm when the end of effective operational lifetime of the part is reached.

SUMMARY

According to one embodiment, a method of diagnosing status of a consumable part of a plasma reaction chamber wherein the consumable part includes at least one conductive element embedded therein, includes the steps of: coupling the conductive element to a power supply so that a bias potential relative to the ground is applied to the conductive element; exposing the consumable part to plasma thereby causing the conductive element to draw a current from the plasma upon exposure of the conductive element to the plasma; measuring the current; and evaluating a degree of erosion of the consumable part due to the plasma based on the measured current.

According to another embodiment, a consumable part of a plasma reaction chamber wherein the consumable part is formed of dielectric material and including a surface to be exposed to plasma, includes: one or more conductive elements embedded in the consumable part; a probe circuit coupled to the conductive elements; and a power supply coupled to the probe circuit and ground to apply a bias potential to the conductive elements relative to the ground, wherein the conductive elements are operative to draw a current from the plasma upon exposure of the conductive element to the plasma and the probe circuit is operative to measure the current.

According to yet another embodiment, a consumable part of a plasma reaction chamber wherein the consumable part is formed of conductive material and including a surface to be exposed to plasma, includes: one or more conductive elements embedded in the consumable part and electrically insulated from the consumable part by a dielectric layer; a probe circuit coupled to the conductive elements; and a power supply coupled to the probe circuit and ground thereby to apply a bias potential to the conductive elements relative to the ground, wherein the conductive elements are operative to draw a current from the plasma upon exposure of the conductive element to the plasma and the probe circuit is operative to measure the current.

BRIEF DESCRIPTION OF THE DRAWINGS

FIGS. 4A-4B show schematic cross sectional views of various embodiments of an edge ring.

FIG. 5 shows a schematic cross sectional diagram of an exemplary embodiment of an upper electrode of the type to be used in the plasma processing chamber in FIG. 1.

FIG. 6 shows a schematic cross sectional diagram of the upper electrode in FIG. 5, taken along the line VI-VI.

DETAILED DESCRIPTION

Figure 1:
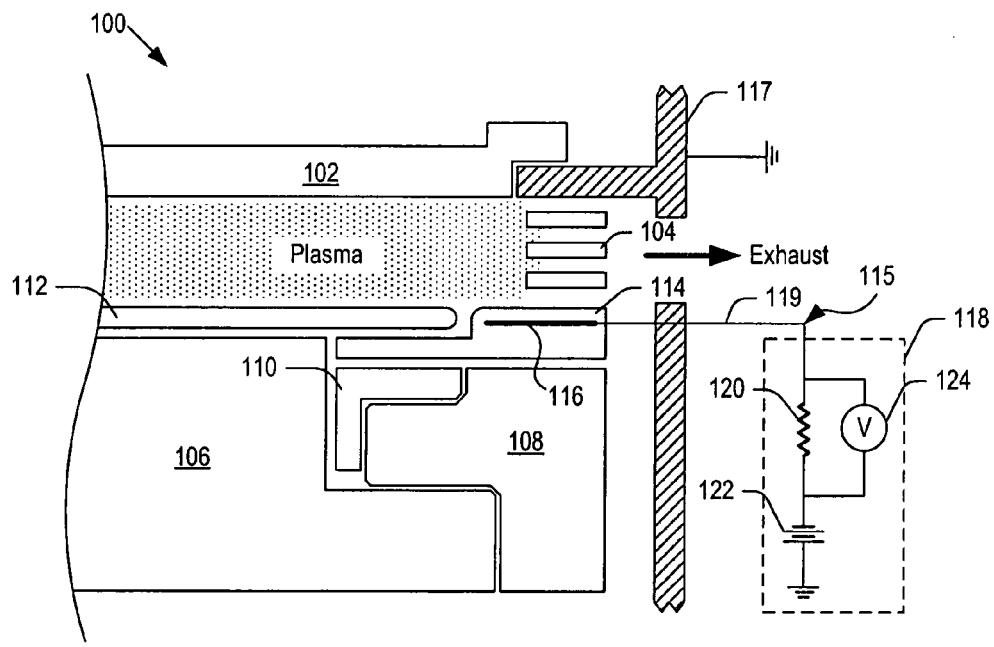
FIG. 1 shows a schematic cross sectional diagram of a plasma processing chamber having a diagnostic sensor in accordance with one embodiment.

Referring now to FIG. 1, there is shown a schematic cross sectional diagram of a plasma processing chamber 100 in accordance with one embodiment. It is noted that the chamber 100 is an exemplary device that generates plasma and includes a diagnostic sensor according to one embodiment. Hereinafter, for brevity, the following discussion is limited to sensors for diagnosing components in the chamber 100. However, it should be apparent to those of ordinary skill that the similar sensor embodiments can be applied to other suitable plasma generating devices.

As depicted, the chamber includes a wall 117 for forming a space within which various components for generating capacitively coupled plasma are disposed. The chamber also includes an electrostatic chuck 106 for holding a substrate 112 in place during operation and an upper electrode 102. The upper electrode 102 and chuck 106 form a pair of electrodes coupled to an RF power source (not shown in FIG. 1) and generate plasma over the top surface of the substrate 112 when powered by the RF source. The chamber 100 also includes a ceramic ring 108, a coupling ring 110 disposed between the ceramic ring and the chuck 106, and an edge ring 114 disposed around the edge of substrate 112. The plasma is confined by confinement rings 104 disposed in the gap between the upper electrode 102 and chuck 106. Some of the gas particles in the plasma pass through the spacing/gaps between the rings 104 and thence are exhausted from the chamber by a vacuum pump.

The edge ring 114 performs several functions, including positioning the substrate 112 relative to the chuck 106 and shielding the underlying components not protected by the substrate itself from being damaged by the plasma. The edge ring 114 also enhances plasma uniformity across the substrate 112. Without the edge ring 114, the substrate 112 electrically defines the outer edge of the chuck and the equipotential lines would curve upward sharply in the vicinity of the substrate edge. As such, without the edge ring 114, the substrate edge would experience a different plasma environment from the plasma environment that exists at the center of the substrate, resulting in poor production yield near the edge. More detailed description of the chamber can be found in commonly owned U.S. Pat. No. 6,986,765.

Due to the aggressive nature of the plasma, the edge ring 114 can wear away over time. As the edge ring 114 wears away, the plasma properties in the vicinity of the damaged regions of the edge ring may change. The changes to the plasma properties in turn may cause the process result to change over time and the chamber may reach a point where the edge ring 114 needs to be replaced.

To monitor the operational condition and structural status of edge ring 114 in real time and to provide an indication of an event, such as the end of useful lifetime of the edge ring, a diagnostic sensor 115 can be coupled to the edge ring 114. The sensor 115 includes a pickup unit or probe 116 and a probe circuit 118 connected to the probe 116 via a conductor wire 119. The probe 116 is embedded in the edge ring 114 such that the probe is completely surrounded by the edge ring 114. In one exemplary embodiment, the probe 116 has the shape of a wire segment or pin. The probe 116 is formed of, but not limited to, conducting material, such as metal, while the edge ring 114 is formed of, but not limited to, electrically insulating or dielectric material.

The probe circuit 118 includes a power supply 122 for applying an electrical potential between the probe 116 and ground. The circuit 118 also includes a resistor 120 and a measuring device 124, such as voltmeter, for measuring the voltage across the resistor or the electrical current flowing through the resistor. The conductor wire 119 is shown to extend from the probe 116 through the chamber wall 117 to the circuit 118. In an alternative embodiment, the circuit 118 may be disposed inside the chamber and the measuring device 124 may be coupled to a display unit that is located outside the chamber wall 117 and operative to display the signal measured by the device 124 to the operator.

The probe 116 is embedded in the edge ring 114 at a depth corresponding to a diagnostic event, such as the end of useful lifetime of the edge ring 114. The probe 116 is biased to a negative dc potential, preferably of 10-15 volts, relative to the ground. During operation, the portion of the edge ring 114 covering the probe 116 from the plasma prevents the energetic positive ions of the plasma from reaching the probe 116. However, upon repeated exposures to the plasma, the covering portion of the edge ring 114 may be eroded and expose the probe 116 to the plasma, causing the probe to draw an ion current from the plasma. The drawn ion current flows through the resistor 120 of the probe circuit 118 and can be measured by measuring the voltage across the resistor. The plasma can be coupled to the ground via the wall 117, upper electrode 102, or other suitable components and complete a path for the ion current drawn by the probe, i.e., the plasma is a source of the ion current and forms a part of the electrical path for the ion current, wherein the ground also forms a part of the electrical path.

In an alternative embodiment, the probe 116 can be biased to a positive dc potential (not shown in FIG. 1), preferably of 10-15 volts, relative to the ground. In this embodiment, the positive terminal of the power supply 122 in FIG. 1 may be connected to the resistor 120 while the negative terminal of the power supply 122 is connected to the ground. The positively biased probe 116 may draw a negative electron current from the plasma when the edge ring 114 is worn out to expose the probe 116 to the plasma. The plasma can be coupled to the ground via the wall 117, upper electrode 102, or other suitable components and complete a path for the electron current drawn by the probe, i.e., the plasma is a source of the electron current and forms a part of the electrical path for the electron current, wherein the ground also forms a part of the electrical path.

Figure 2:
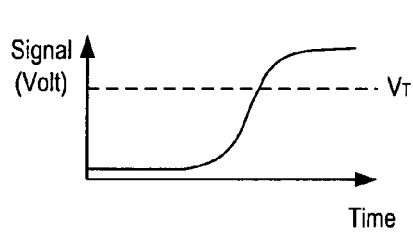
FIG. 2 shows an exemplary plot of signal from the diagnostic sensor in FIG. 1 as a function of time.

FIG. 2 shows an exemplary plot of signal from the measuring device 124 in FIG. 1 as a function of plasma exposure time. As the portion of the edge ring 114 covering the probe 116 from the plasma is worn out, the ion current flowing through the resistor 122, or, equivalently, the voltage across the resistor measured by the device 124 may suddenly increase, as depicted in FIG. 2. This sudden increase in signal intensity may be used as an indicator of the point when the probe 116 is exposed to the plasma. In one embodiment, a warning or notification requiring operator attention or intervention may be triggered when the voltage increases to a preset threshold voltage $V_T$ that corresponds to a diagnostic event, such as the end of effective operational lifetime of the edge ring 114. In another embodiment, warning or notification may be triggered when the voltage shows a sudden change in value. Thus, by monitoring the signal from the measuring device 124, an in situ diagnosis of condition, such as degree of erosion, and performance of the edge ring 114 can be performed in real time.

As discussed above, the probe 116 may be biased to a positive dc potential relative to the ground and draw negative electron currents. In such a case, the vertical axis of the plot in FIG. 2 may represent the absolute value of the voltage across the resistor 120.

Figure 3B:
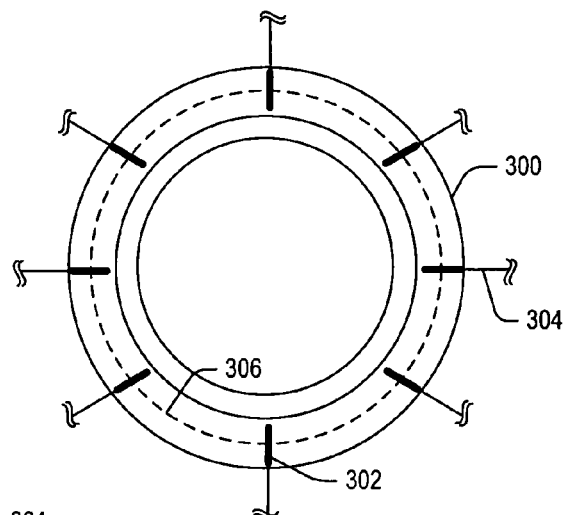
FIGS. 3A-3B show schematic side and top cross sectional views of an edge ring in accordance with another embodiment.
Figure 3A:
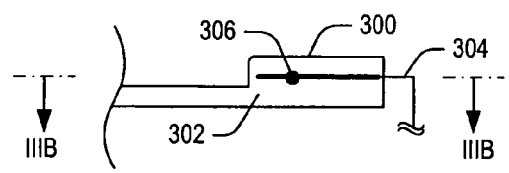

In one exemplary embodiment, the sensor 115 may include multiple probe pins embedded in the edge ring 114 in order to provide redundancy or to monitor the overall integrity of the edge ring. FIG. 3A shows a schematic side cross sectional view of an edge ring 300 within which multiple probes 302 are embedded. FIG. 3B shows a schematic top cross sectional view of the edge ring 300 with eight probes 302, taken along the line IIIA-IIIB. For brevity, the probe circuit coupled to the probes via conductor wire 304 is not shown in FIG. 3A.

As depicted in FIGS. 3A-3B, multiple probes or probe pins 302 are arranged circumferentially at a preset angular interval about the central axis of the edge ring 300. It is noted that any other suitable number of probes 302 may be embedded in the edge ring 300. In another exemplary embodiment, the probes 302 may be electrically connected to each other via an optional connection wire 306, wherein the connection wire 306 may be formed of electrically conducting material and embedded in the edge ring 300. In this embodiment, all of the probes 302 may be coupled to the probe circuit.

The shape, dimension, and material compositions of the probe are selected according to the type of application thereof. In one exemplary embodiment, the diagnostic sensor may include a plurality of thin plates coupled to a probe circuit, each plate having a generally polygonal or circular plate/disk shape. For instance, FIG. 4A shows a schematic cross sectional view of an exemplary embodiment of an edge ring 400. As depicted, the multiple probes 402 are circumferentially arranged and embedded in the edge ring 400. Each probe 402 has a flat circular disk shape and coupled to a probe circuit (not shown in FIG. 4A) via a conductor wire 404. It is noted that the probe 402 may have other suitable shapes, such as rectangular.

Optionally, the multiple probes 402 embedded in the edge ring 400 may be connected to each other by a connection wire 406, wherein the connection wire 406 may be formed of electrically conducting material and embedded in the edge ring. In this embodiment, all of the probes may be coupled to the probe circuit via a conductor wire.

FIG. 4B shows a schematic cross sectional view of another embodiment of an edge ring 410. As depicted, a probe 412 having an annular shape is embedded in the edge ring 410. For brevity, the probe circuit coupled to the probe 412 via a conductor wire 404 is not shown in FIG. 4B.

The diagnostic sensors of FIGS. 1-4B can be applied to other suitable components, such as confinement rings, that can be eroded by actions of the plasma and made of electrically insulating or dielectric material. Signals from multiple diagnostic sensors associated with these components can be simultaneously monitored to diagnose the conditions of the components in real time. For components made of conducting or semiconductor material, such as the upper electrode 102 (FIG. 1), the probe can be surrounded by dielectric material in order to prevent a direct contact between the probe and host component in which the probe is embedded, as discussed in conjunction with FIGS. 5-7B. Hereinafter, for the purpose of illustration, an upper electrode is described as an exemplary host component formed of conducting material.

FIG. 5 shows a schematic cross sectional diagram of an exemplary embodiment of an upper electrode 500 that might be used in the plasma processing chamber in FIG. 1. FIG. 6 shows a schematic cross sectional diagram of the upper electrode 500. For brevity, the detailed configuration of the electrode, such as gas injection mechanism, is not shown in FIGS. 5-6. As depicted, the upper electrode 500 is associated with a diagnostic sensor 501 that includes one or more probe units 503 embedded in the upper electrode. Each probe unit 503 has a probe 502 including a pin or wire segment formed of conducting material, such as metal, and an insulating layer 504 surrounding the probe to electrically insulate the probe from the upper electrode 500. The insulating layer 504 may be formed by, for example, a coating of dielectric material on the probe 502. The sensor 501 also includes a sensor circuit 506 and one or more conductor wires 508, each of the conductor wires 508 being coupled to the sensor circuit 506 and a corresponding one of the probes 502. The conductor wires 508 can be electrically insulated from the upper electrode 500.

In one exemplary embodiment, each probe 502 can be individually coupled to the probe circuit 506 via a conductor wire 508. In another exemplary embodiment, the probes 502 can be electrically connected to each other by an optional connection wire 506, wherein the wire 506 is embedded in the upper electrode 500 and insulated from the upper electrode by an insulating layer, such as dielectric coating, surrounding the wire 506. In this embodiment, all of the probes 502 are coupled to the probe circuit 506. The probe circuit 506 may have components and operational mechanisms similar to those of the circuit 118 in FIG. 1.

Figure 7A:
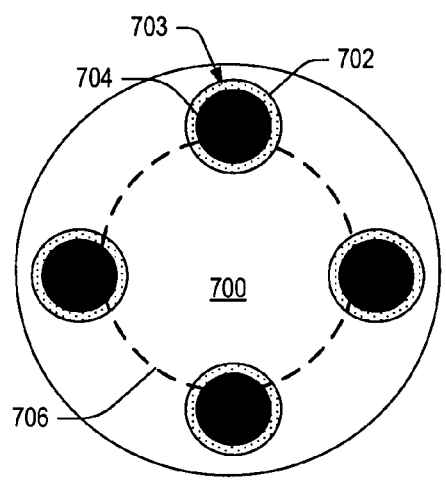
FIGS. 7A-7C show schematic cross sectional diagrams of various exemplary embodiments of an upper electrode of the type to be used in the plasma processing chamber in FIG. 1.

In yet another exemplary embodiment, each probe can include a thin plate that is formed of, but not limited to, conducting material and has a generally round or polygonal shape. For instance, FIG. 7A shows a schematic cross sectional view of an exemplary embodiment of an upper electrode 700, taken along a direction parallel to the line VI-VI (FIG. 5). As depicted, each of the multiple probe units 703 embedded in the upper electrode 700 includes a probe 704 having a flat circular disk shape and an insulating layer 702 surrounding the probe to electrically insulate the probe from the upper electrode 700. It is noted that the probe 704 may have other suitable shapes, such as rectangular. It is also noted that any suitable number of probes may be used in the upper electrode.

Optionally, the multiple probes 704 may be connected to each other by a connection wire 706 that is similar to the connection wire 506 (FIG. 5). In this embodiment, all of the probes are coupled to the probe circuit via a conductor wire.

Figure 7B:
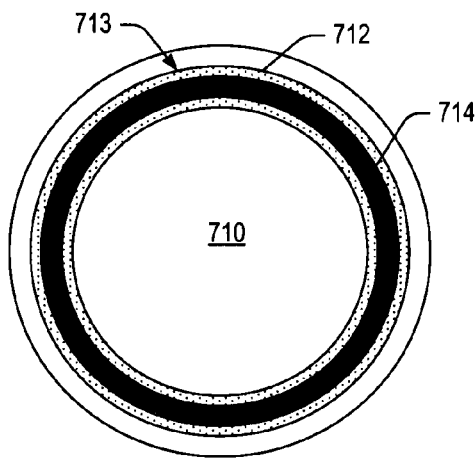

In still another exemplary embodiment, the probe embedded in the upper electrode may have a generally annular shape, as shown in FIG. 7B. FIG. 7B shows a schematic cross sectional view of an upper electrode 710. As depicted, a probe unit 713 embedded in the upper electrode 710 includes an annular probe 714 and an insulating layer 712 surrounding the probe 714 and electrically insulating the probe 714 from the upper electrode 710. The probe 714 may be formed of a conducting material, such as metal, and coupled to a probe circuit similar to the circuit 118 in FIG. 1.

Figure 7C:
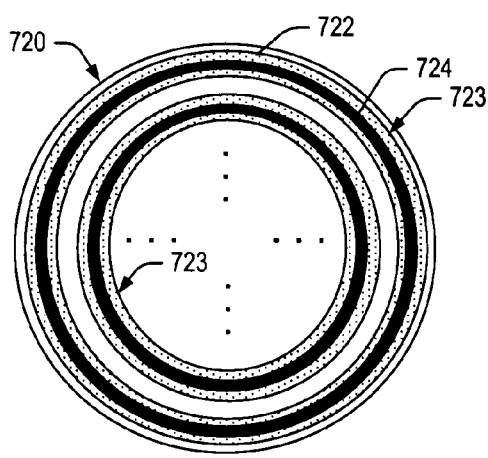

FIG. 7C shows a schematic top cross sectional view of another exemplary embodiment of an upper electrode 720. As depicted, multiple probe units 723 may be concentrically embedded in an upper electrode 720 and each probe unit 723 includes an annular probe 724 and an insulating layer 722 surrounding the probe and electrically insulating the probe 724 from the upper electrode 720. In the case where the upper electrode 720 includes multiple gas holes to have a showerhead configuration, the radial spacing between probe units can include gas outlets therein. The insulating layer 722 and probe 724 may be respectively formed of materials similar to those of layer 712 and probe 714.

It is noted that the probes described in FIGS. 3A-7C can be biased to a positive dc potential, preferably of 10-15 volts, relative to the ground. For instance, the positive terminal of the power supply in FIG. 5 is connected to the resistor while the negative terminal of the power supply is connected to the ground. For brevity, the probes positively biased with respect to the ground are not described in detail. However, it should be apparent that the operational and structural features of the sensor embodiments having negatively biased probes are similar to those of the sensor embodiments having positively biased probes.

While the invention has been described in detail with reference to specific embodiments thereof, it will be apparent to those skilled in the art that various changes and modifications can be made, and equivalents employed, without departing from the scope of the appended claims.

What is claimed is:

1. A consumable part of a plasma reaction chamber, the consumable part including a surface to be exposed to plasma, comprising:
    conductive elements embedded in the consumable part and electrically coupled to each other;
    a probe circuit coupled to the conductive elements; and
    a power supply coupled to the probe circuit and ground to apply a bias potential to the conductive elements relative to the ground,
    wherein the conductive elements are operative to draw a current from the plasma upon exposure of the conductive elements to the plasma and the probe circuit is operative to measure the current, wherein the consumable part is an electrode for generating plasma or a dielectric material selected from the group of edge ring and confinement ring.

2. The consumable part of claim 1, wherein the power supply is a DC power source.

3. The consumable part of claim 1, wherein the probe circuit includes a resistor and a voltmeter to measure an electrical potential across the resistor.

4. The consumable part of claim 3, wherein the voltmeter is connected to the resistor in parallel.

5. The consumable part of claim 1, wherein each of the conductive elements has a shape selected from the group consisting of pin, polygonal, circular, and annular.

6. The consumable part of claim 1, wherein the conductive elements are electrically connected to each other by a conductive wire.

7. The consumable part of claim 1, wherein the consumable part is formed of conductive material and the conductive elements are embedded in the consumable part and electrically insulated from the consumable part by a dielectric layer.

8. A method of processing a semiconductor substrate in a plasma reaction chamber including the consumable part of claim 1, comprising plasma processing the semiconductor substrate.

9. The consumable part of claim 1, wherein the power supply is operable to supply a bias potential of 10 to 15 volts relative to the ground to the conductive elements.

10. The consumable part of claim 1, wherein the power supply is connected in series to the probe circuit.

11. The consumable part of claim 1, wherein the conductive elements are embedded at a depth corresponding to a diagnostic event.

12. The consumable part of claim 11, wherein the diagnostic event is end of useful lifetime of the consumable part.

13. The consumable part of claim 1, wherein the conductive elements are annular conductive elements embedded in the consumable part.

\* \* \* \* \*